United States Patent [19]

Schmidt et al.

[11] 4,093,442
[45] June 6, 1978

[54] SYNERGISTIC HERBICIDAL COMPOSITIONS COMPRISING 3-(BENZTHIAZOL-2-yl)-1,3-DIMETHYLUREA AND A SUBSTITUTED DIPHENYL ETHER

[75] Inventors: Robert Rudolf Schmidt, Cologne; Lothar Rohe, Wuppertal, both of Germany

[73] Assignee: Bayer Aktiengesellschaft, Leverkusen, Germany

[21] Appl. No.: 692,169

[22] Filed: Jun. 2, 1976

[30] Foreign Application Priority Data

Jun. 19, 1975 Germany ............... 2527394

[51] Int. Cl.$^2$ ........................ A01N 9/12
[52] U.S. Cl. ........................ 71/90; 71/105
[58] Field of Search ........................ 71/90

[56] References Cited

U.S. PATENT DOCUMENTS

| | | | |
|---|---|---|---|
| 2,756,135 | 7/1956 | Searle | 71/90 |
| 3,845,069 | 10/1974 | Schafer et al. | 71/90 X |
| 3,950,379 | 4/1976 | Bayer et al. | 71/90 X |
| 3,954,829 | 5/1976 | Rohe et al. | 71/105 |
| 3,966,453 | 6/1976 | Takahashi et al. | 71/105 X |

*Primary Examiner*—Joseph Paul Brust
*Attorney, Agent, or Firm*—Burgess, Dinklage & Sprung

[57] ABSTRACT

Herbicidal compositions containing as active ingredients (1) 3-benzthiazol-2-yl)-1,3-dimethylurea, which has the formula

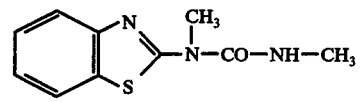

and (2) 2,6-dichloro-4-trifluoromethyl-4-'-cyano-diphenyl ether, which has the formula

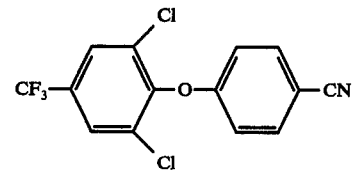

alone or in admixture with a solid or liquid or liquefied gaseous diluent or carrier, exhibit outstanding synergistic herbicidal activity and selectivity.

10 Claims, No Drawings

SYNERGISTIC HERBICIDAL COMPOSITIONS COMPRISING 3-(BENZTHIAZOL-2-yl)-1,3-DIMETHYLUREA AND A SUBSTITUTED DIPHENYL ETHER

The present invention relates to new herbicidal compositions comprising 3-(benzthiazol-2-yl)-1,3-dimethylurea and a substituted diphenyl ether.

It is known that 3-(benzthiazol-2-yl)-1,3-dimethylurea can be used as a selective herbicide in cereals from Belgian Pat. No. 687,019. Furthermore, it is known that substituted diphenyl ethers, for example 2,6-dichloro-4-trifluoromethyl-4'cyano-diphenyl ethers can be used as herbicides from German Offenlegungsschrift (German Published Specification) No. 2,333,848. The herbicidal activity of the aforesaid compounds is, however, not always fully satisfactory, especially when used against weeds which are usually difficult to combat.

The present invention provides a herbicidal composition containing as active ingredients (1) 3-benzthiazol-2-yl)-1,3-dimethylurea, which has the formula

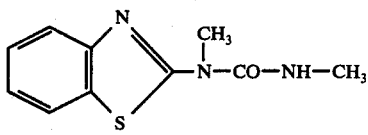

and (2) 2,6-dichloro-4-trifluoromethyl-4-'-cyano-diphenyl ether, which has the formula

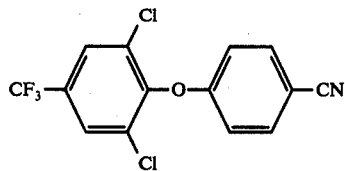

alone or in admixture with a solid or liquid or liquefied gaseous diluent or carrier.

The compositions of this invention have been found to exhibit a particularly broad and selective herbicidal activity in cereal cultures.

Surprisingly, the activity of the active compound combination according to the invention is substantially greater than the sum of the actions of the individual active compounds. An unforeseeable genuine synergistic effect exists, and not just a supplementation of the action. Accordingly, the active compound combination represents a valuable enrichment of the art.

The active compounds contained in the compositions according to the present invention are already known from German Offenlegungsschrift (German Published Specification) No. 2,333,848 and Belgian Patent Specification No. 687,019.

The synergistic effect manifests itself particularly strongly at certain combination ratios. However, the weight ratios of the active compounds in the present compositions can vary within fairly broad ranges. In general, 0.05 to 10 parts by weight, preferably 0.1 to 5 parts by weight, of the active compound of the formula (II) are used per part by weight of the active compound of the formula (I).

The active compound combination according to the invention exhibits a very good action against weeds and wild grasses without harming the cereal. It can, therefore, be used for the selective combating of weeds in cereal cultures.

Examples of cereal cultures are cultures of oats, barley, wheat, rye and corn.

Weeds which may be concerned are, in particular: dicotyledons such as mustard (Sinapis), cress (Lepidium), cleavers (Galium), chickweed (Stellaria), camomile (Matricaria), mayweed (Anthemis), gallant soldier (Galinsoga), goosefoot (Chenopodium), annual nettle (Urtica), groundsel (Senecio), pigweed (Amaranthus), purslane (Portulaca), cocklebur (Xanthium), bindweed (Convolvulus), morning glory (Ipomoea), knotweed (Polygonum), sesbania (Sesbania), ragweed (Ambrosia), spear thistle (Cirsium), common thistle (Carduus), sow thistle (Sonchus), nightshade (Solanum), field cress (Rorippa), toothcup (Rotala), lindernia (Lindernia), deadnettle (Lamium), speedwell (Veronica), mallow (Abutilon), emex (Emex), thornapple (Datura), violet (Viola), hemp-nettle (Galeopsis), poppy (Papaver) and knapweed (Centaurea), and monocotyledons such as barnyard grass (Echinochloa), foxtail (Setaria), wild millet (Panicum), crabgrass (Digitaria), timothy (Phleum), bluegrass (Poa) fescue (Festuca), goosegrass (Eleusine), signalgrass (Brachiaria), ryegrass (Lolium), cheat (Bromus), oats (Avena), flatsedge (Cyperus), sorghum (Sorghum), quackgrass (Agropyron), Bermuda grass (Cynodon), Monocharia, fimbristylis, arrowhead (Sagittaria), spikerush (Eleocharis), bulrush (Scirpus), paspalum (Paspalum), Ischaemum, gooseweed (Sphenoclea), crowfoot grass (Dactyloctenium), redtop (Agrostis), meadow foxtail (Alopercurus) and silky bent-grass (Apera).

The good activity of the active compound combinations according to the invention against weeds which are normally difficult to combat, such as, for example, cleavers (*Galium aparine*), and against wild grasses which are difficult to combat, such as, for example, foxtail grass (*Alcopercurus myosuroides*) should be singled out particularly. It is of particular advantage that such weeds and wild grasses which are usually difficult to combat can be combated at the same time with the active compound combination according to the invention.

The active-compound combination according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chlorethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active-compound combination according to this invention can be present in the formulations as a mixture with other active compounds.

The formulations in general contain from 0.1 to 95 per cent by weight of total active compounds, preferably from 0.5 to 90 per cent.

The active compound combination can be used as such, in the form of its formulations or as the use forms prepared therefrom, such as ready-to-use solutions, emulsions, foams, suspensions, powders, pastes and granules. They may be used in the customary manner, for example by dusting, atomizing, spraying, watering and scattering.

The amounts used of the active compound combination according to the present invention can be varied within a fairly wide range. In general, they are from 0.05 to 10 kg/ha, preferably from 0.05 to 5 kg/ha.

The active compound combination according to the invention can be used before and/or after the emergence of the plants.

The present invention therefore also provides a method of combating weeds which comprises applying to the weeds or a weed habitat a composition of the present invention.

The present invention further provides methods of yielding crops, especially cereal crops, protected from damage by weeds by being grown in areas in which immediately prior to and/or during the time of growing a composition of the present invention was applied. It will be seen that the usual methods of providing a harvested crop may be improved by the present invention.

The good herbicidal action of the active compound combination of this invention can be seen from the biotest Examples which follow. While the individual active compounds show weaknesses in the herbicidal action, the combination exhibits a very broad action against weeds, which goes beyond a simple additive action.

A synergistic effect exists with herbicides whenever the herbicidal action of the active compound combination is greater than that of the individually applied active compounds.

The action to be expected for a given combination of two herbicides can be calculated as follows (see Colby, S.R., "Calculating synergistic and antagonistic responses of herbicide combinations", Weeds 15, pages 20-22, 1967):

If $X = \%$ damage of herbicide A when using $p$ kg/ha and $Y = \%$ damage by herbicide B when using a $q$ kg/ha and $E = $ the expected damage of herbicides A and B when using $p$ and $q$ kg/ha then $$E = X + Y - (X \cdot Y/100).$$

If the actual damage is greater than calculated, the action of the combination is super-additive, that is to say a synergistic effect exists.

The tables of Examples A and B show unambiguously that the found herbicidal action of the active compound combination according to the invention against weeds is greater than that calculated, that is to say a genuine synergistic effect exists.

EXAMPLE A

Pre-emergence Test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was rated in % damage in comparison to the development of the untreated control. The figures denote:

0% = no action (like untreated control)
100% = total destruction.

The active compounds, the amounts applied and the results can be seen from the table which follows:

Table A

| Active compound or active compound combination | Pre-emergence test | | | |
|---|---|---|---|---|
| | Amount used kg/ha | Wheat | Galium aparine found* | calculated* |
| (I) (known) | 1.5 | 0 | 0 | |
| | 1 | 0 | 0 | |
| | 0.5 | 0 | 0 | |
| (II) (known) | 0.5 | 0 | 20 | |
| | 0.25 | 0 | 0 | |
| | 0.125 | 0 | 0 | |
| (I) + (II) according to the invention | 0.5 + 0.5 | 0 | 90 | 20 |
| | 0.5 + 0.125 | 0 | 80 | 0 |
| | 1.0 + 0.5 | 0 | 90 | 20 |
| | 1.5 + 0.5 | | 90 | 20 |
| | 1.5 + 0.25 | | 60 | 0 |

*found = damage found
*calculated = damage calculated from the formula given earlier

EXAMPLE B

Post-emergence Test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was then diluted with water to the desired concentration.

Test plants which had a height of 5-15 cm were sprayed with the preparation of the active compound in such a way as to apply the amounts of active compound per unit area which are indicated in the table. The concentration of the spray liquor was so chosen that the amounts of active compound shown in the table were applied in 2,000 l of water/ha. After three weeks, the degree of damage to the plants was rated in % damage in comparison to the development of the untreated control. The figures denote:

0% = no action (like untreated control)
100% = total destruction.

The active compounds, the amounts applied and the results can be seen from the table which follows:

Table B

| Active compound or active compound combination | Post-emergence test | | | |
|---|---|---|---|---|
| | Amount used kg/ha | Wheat | Alopecurus found* | myosuroides calculated* |
| (I) (known) | 1.5 | 0 | 70 | |
| | 1.0 | 0 | 40 | |
| | 0.5 | 0 | 0 | |
| (II) (known) | 0.5 | 0 | 100 | |
| | 0.25 | 0 | 90 | |
| | 0.125 | 0 | 60 | |
| (I) + (II) according to the invention | 0.5 + 0.25 | 0 | 100 | 90 |
| | 0.5 + 0.125 | 0 | 90 | 60 |
| | 1.0 + 0.25 | 0 | 100 | 94 |
| | 1.0 + 0.125 | 0 | 90 | 76 |
| | 1.5 + 0.125 | 0 | 100 | 88 |

*found = damage found
*calculated = damage calculated from the formula given earlier It will be understood that the specification and examples are illustrative but not limitative of the present invention and that other embodiments within the spirit and scope of the invention will suggest themselves to those skilled in the art.

What is claimed is:

1. A herbicidal composition containing as active ingredients synergistically effective amounts of (1) 3-(benzthiazol-2-yl)-1,3-dimethylurea, of the formula

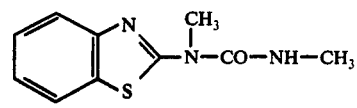

and (2) 2,6-dichloro-4-trifluoromethyl-4'-cyano-diphenyl ether of the formula

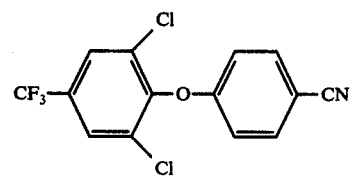

said composition containing (1) the urea and (2) the diphenyl ether in a ratio by weight of 1:0.1 to 1.

2. A herbicidal composition as claimed in claim 1 containing from 0.1 to 95% of total active ingredients, by weight.

3. A herbicidal composition as claimed in claim 2, containing from 0.5 to 90% of total active ingredients, by weight.

4. A herbicidal composition as claimed in claim 1, wherein said active ingredients are in admixture with a liquid, solid, or liquefied gaseous synergistically acceptable carrier.

5. A method of combating galium aparine which comprises applying to the galium aparine or its habitat a herbicidal composition as claimed in claim 1, the active ingredients of the composition being applied to the weed or its habitat in a total amount between 0.05 and 5 kg/ha.

6. A method as claimed in claim 5 in which the active compounds are applied to an area of cereal cultivation.

7. A method as claimed in claim 5 wherein the composition is applied to the galium aparine habitat before emergence of the galium aparine.

8. A method according to claim 5 wherein the composition is applied to the galium aparine or galium aparine habitat after emergence of the galium aparine.

9. A method as claimed in claim 6 wherein the composition is applied to the galium aparine habitat before emergence of the galium aparine.

10. A method according to claim 6 wherein the composition is applied to the galium aparine or galium aparine habitat after emergence of the galium aparine.

* * * * *